US00PP17153P2

(12) United States Plant Patent
Egger

(10) Patent No.: US PP17,153 P2
(45) Date of Patent: Oct. 10, 2006

(54) ***HEUCHERA* PLANT NAMED 'BLOOD RED'**

(50) Latin Name: *Heuchera ((sanguinea×cylindrica)×sanguinea)*
Varietal Denomination: Blood Red

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 10 days.

(21) Appl. No.: 11/155,231

(22) Filed: Jun. 16, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct hybrid of *Heuchera* plant characterized by very large, deep red flowers, green leaves, and a compact habit.

1 Drawing Sheet

Botanical denomination: *Heuchera* ((*sanguinea*×*cylindrica*)×*sanguinea*).

Variety designation: 'Blood Red'.

The present invention relates to a new and distinct cultivar of *Heuchera* and given the cultivar name of 'Blood Red'. *Heuchera* is in the family Saxifragaceae. *Heuchera* 'Blood Red' originated from a cross between *Heuchera* 'Strawberry Candy' (U.S. Plant Pat. No. 12,195) as the seed parent, and *Heuchera sanguinea* Black Red (an unpatented, proprietary plant) as the pollen parent.

This new *Heuchera* is distinguished by:

1. Very large, blood red flowers;
2. Small leaves that are often speckled yellow;
3. Low compact habit;
4. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The photograph shows a one-year-old plant of *Heuchera* 'Blood Red' growing in a one gallon container in the shade house.

DETAILED PLANT DESCRIPTION

The following is a detailed description of the new *Heuchera* cultivar based on observations taken in May of a two-year-old specimen grown the ground in the garden beds in full sun in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 5 to 9.
*Size.*—13 cm tall from the ground to the top of the foliage and 30 cm wide.
*Habit.*—Low mound.
*Vigor.*—Good.
*Roots.*—Fibrous, freely branching, fine, and white in color. Roots develop easily from cuttings.

Leaf:

*Type.*—Simple.
*Arrangement.*—Rosette.
*Shape.*—Broadly ovate to orbicular.
*Lobing division.*—5 to 7 lobes, shallow and rounded, each notched 1 to 2 times.
*Venation.*—Palmate.
*Margins.*—Cuneate, glandular.
*Apex.*—Mucronulate.
*Base.*—Cordate, lobes overlapping at the base and cupping up.
*Blade size.*—Grows to 5.8 cm long and 5.5 cm wide.
*Surface texture.*—Glandular on both sides.
*Petiole description.*—Grows to 11.5 cm long and 2 mm wide with the surface having long and short glandular hairs, color is Yellow Green 146B.
*Leaf color.*—Topside — Green 137A with a slight veil, Green 138D, and speckled variegation on some leaves of Yellow Green 154C. Bottom side — Green 138B.

Inflorescence:

*Type.*—Thyrse.
*Number of flowers.*—About 59 per thyrse.
*Number of thyrse in spring.*—15 in the first flush, repeat blooms.
*Peduncle.*—With 0 to 1 much reduced cauline leaf, grows to 40 cm tall and 2.3 mm wide at the base, brown in color, Greyed Orange 177A, with glandular hairs.

*Pedicel.*—Variable in length, Greyed Orange 177A, with glandular hairs.

*Bloom period.*—May with sporadic repeat bloom Canby, Oreg.

Flower bud:

*Size.*—4 mm wide and 8.8 mm long.

*Description.*—Glandular, ovoid, down facing.

*Color.*—Closest to Red 46A with the base lighter, Red 45C, and the tips darker, Red 53A.

Flower:

*Type.*—Perfect, zygomorphic.

*Shape.*—Campanulate.

*Size.*—10 mm long and 11 mm wide.

*Petal description.*—5, very small, inside the calyx obes, 2 mm long and 0.5 mm wide, oblanceolate with a clawed base, tip acute, margin entire, backs with glandular hairs, slightly reflexed, Red 52B.

*Calyx description.*—10 mm long and 11 mm wide, campanulate, 5 broadly ovate lobes, spreading open, divided ⅓ way to the base, glandular on both sides, tip acute, margin entire.

*Calyx and overall flower color.*—Inside: Red 53B on the lobes to Red 53A on tips, tube Red 52B Outside: Red 53B on the tube and lobes to Red 53A on tips. Past maturity: Red 53A with tips Greyed Purple 187A.

*Stamen description.*—5 in number, 2.5 mm long, filaments 1.5 mm long, Red 52D, anthers before dehiscence Yellow 7B, oval and about 0.5 mm long, pollen Yellow 7A.

*Pistil description.*—4 mm long, Yellow Green 154C, 2 parted, ovary 2 mm, style 2 mm.

*Fragrance.*—None.

*Lastingness.*—Each thyrse blooms for about 3 weeks on the plant.

Fruit:

*Type.*—Two-beaked ovoid capsule.

*Color.*—Brown 200D.

Seed:

*Shape.*—Linear.

*Size.*—2 mm. long.

*Color.*—Black 202A.

Pest and Disease Tolerance: Excellent disease resistance to powdery mildew, the common problem of *Heuchera.* Susceptible to *Heuchera* rust and root weevils.

COMPARISON TO SIMILAR *HEUCHERA*

Compared to *Heuchera* 'Strawberry Candy' (U.S. Plant Pat. No. 12,195), the seed parent, this new variety has red rather than pink flowers.

Compared to *Heuchera sanguinea* Black Red, the pollen parent, the new variety has a larger habit and flowers. The flower size, color, and inflorescence shape differ. The new variety has larger, clearer red flowers in a wand type arrangement while the pollen parent has smaller, very dark red flowers in a normal thyrse.

I claim:

1. A new and distinct hybrid of *Heuchera* plant as herein illustrated and described.

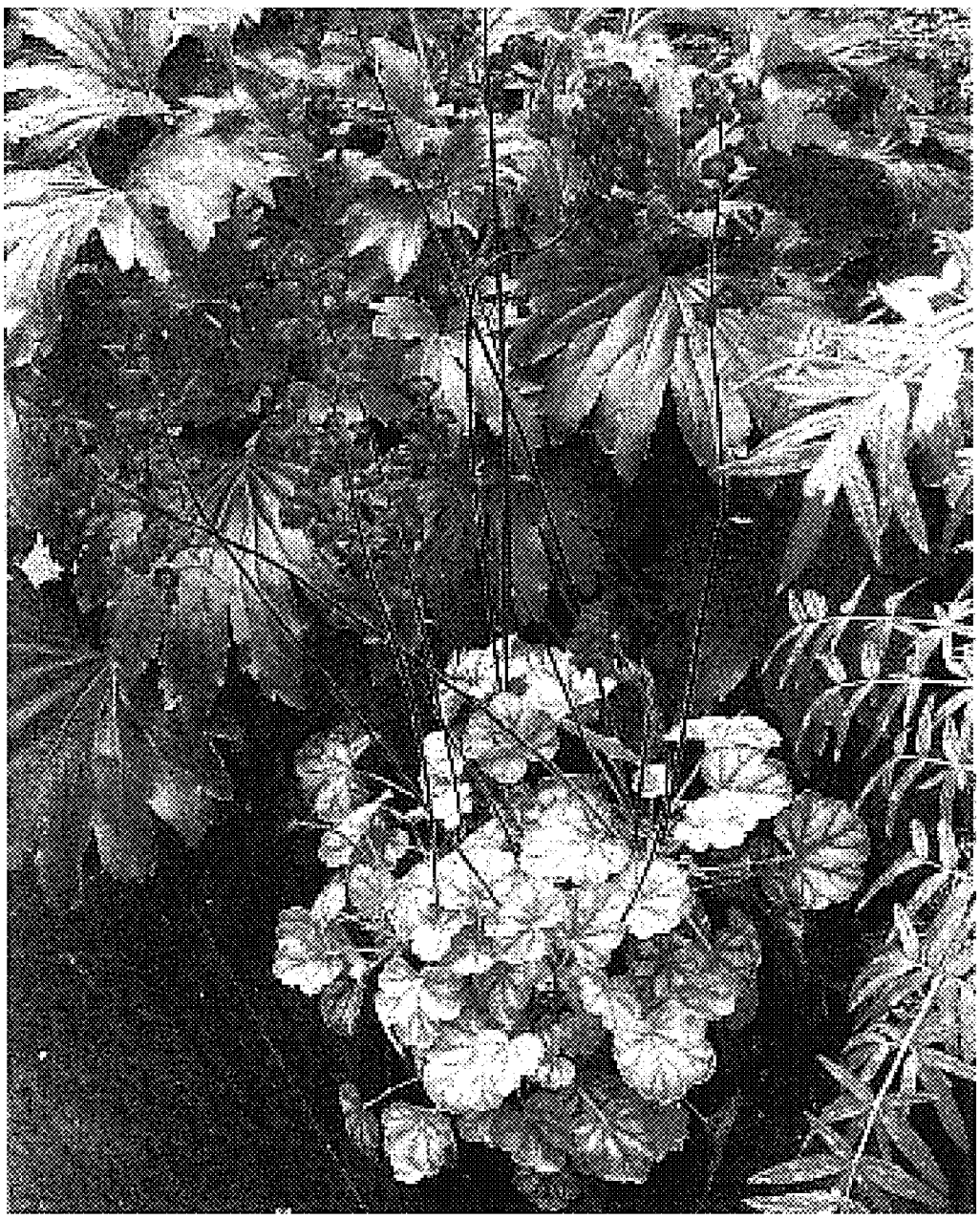

* * * * *